United States Patent
Crozet et al.

(10) Patent No.: US 6,616,695 B1
(45) Date of Patent: Sep. 9, 2003

(54) IMPLANT FOR REPLACING A VERTEBRA

(75) Inventors: Yves Crozet, Seynod (FR); Christian Baccelli, Saint Médard d'Eyrans (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/601,180

(22) PCT Filed: Jan. 29, 1999

(86) PCT No.: PCT/FR99/00183

§ 371 (c)(1),
(2), (4) Date: Sep. 15, 2000

(87) PCT Pub. No.: WO99/38462

PCT Pub. Date: Aug. 5, 1999

(30) Foreign Application Priority Data

Jan. 30, 1998 (FR) .............................................. 98 01053

(51) Int. Cl.⁷ .................................................. A61F 2/02
(52) U.S. Cl. ...................................... 623/17.11; 606/61
(58) Field of Search ........................... 623/17.11, 17.12, 623/17.15, 17.16; 606/61

(56) References Cited

U.S. PATENT DOCUMENTS

| | | | |
|---|---|---|---|
| 4,554,914 A | 11/1985 | Kapp et al. ..................... 128/92 |
| 5,290,312 A | 3/1994 | Kojimoto et al. ............. 623/17 |
| 5,702,455 A | 12/1997 | Saggar | |
| 5,723,013 A | 3/1998 | Jeanson et al. ................ 623/17 |
| 5,776,197 A | 7/1998 | Rabbe et al. | |
| 6,015,436 A | * 1/2000 | Schonhoffer ............. 623/17.16 |
| 6,193,755 B1 | 2/2001 | Metz-Stavenhagen et al. |
| 6,200,348 B1 | * 3/2001 | Biedermann et al. .... 623/17.16 |

FOREIGN PATENT DOCUMENTS

| | | |
|---|---|---|
| DE | 30 23 942 A1 | 1/1982 |
| DE | 40 12 622 C1 | 7/1991 |
| DE | 195 19 101 A1 | 11/1996 |
| DE | 196 22 827 A1 | 12/1997 |
| EP | 0 567 424 A1 | 4/1993 |
| WO | 92/01428 | 2/1992 |
| WO | 94/18913 | 9/1994 |

OTHER PUBLICATIONS

Soviet Patents Abstracts; Section PQ, Week 942831 Aug. 1994 Derwent Publications Ltd., London, GB; AN 94-232473 XP002103980 & SU 1 810 051 A (AFA-NASEV), Apr. 23, 1993.

* cited by examiner

Primary Examiner—David J. Isabella
(74) Attorney, Agent, or Firm—Lerner, David, Littenberg, Krumholz & Mentlik, LLP

(57) ABSTRACT

The invention concerns an implant (2) for replacing a vertebra at least-partially, consisting of two parts (4, 6) adapted to be mutually connected while enabling the adjustment of the implant total dimension (L), each part having an invariable dimension (m, f) homologous with the implant total dimension (L). The parts (4, 6) form a screw-nut connection with each other.

23 Claims, 2 Drawing Sheets

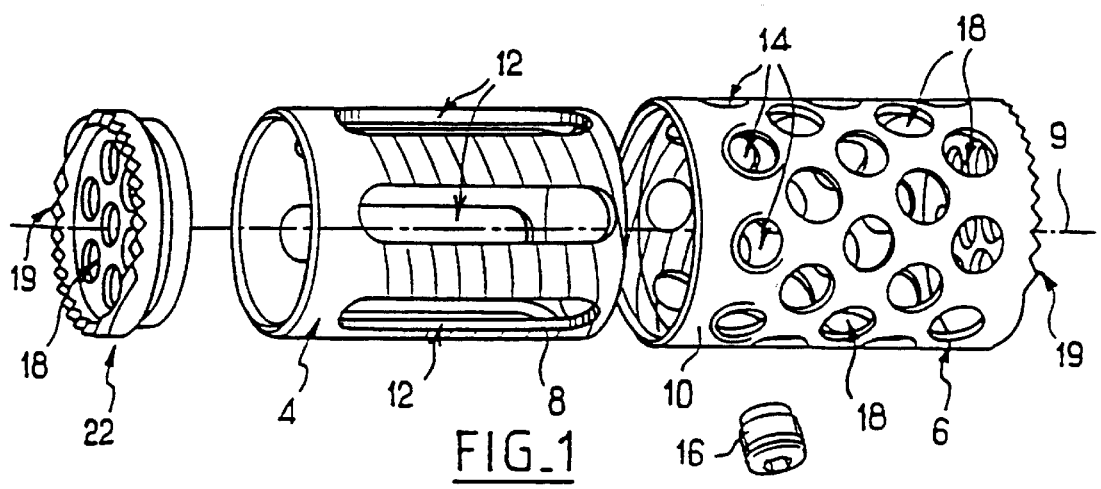
FIG_1
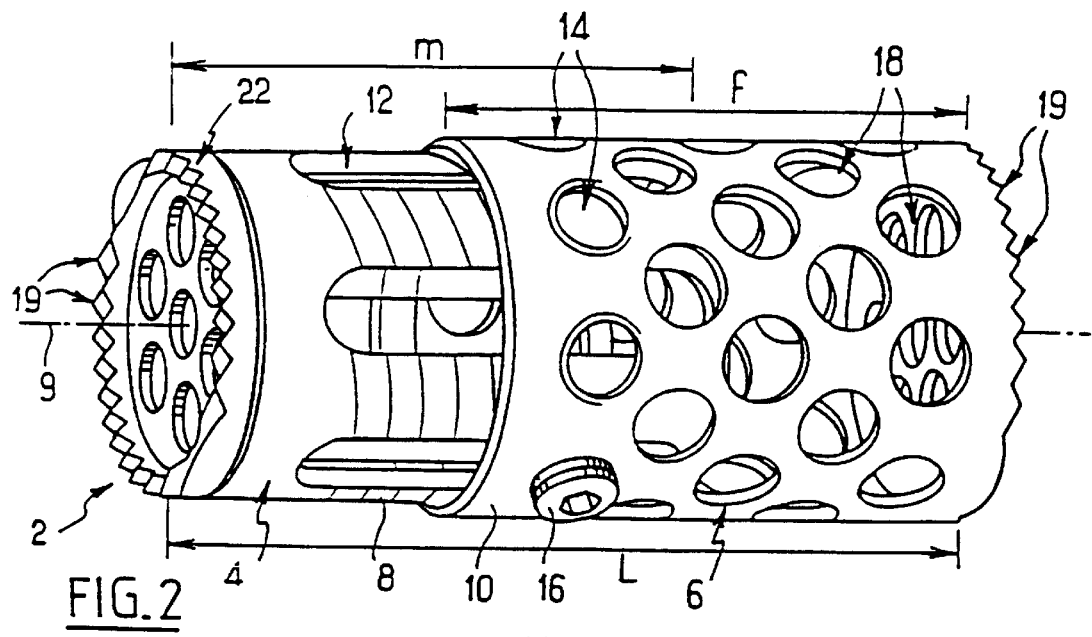
FIG_2
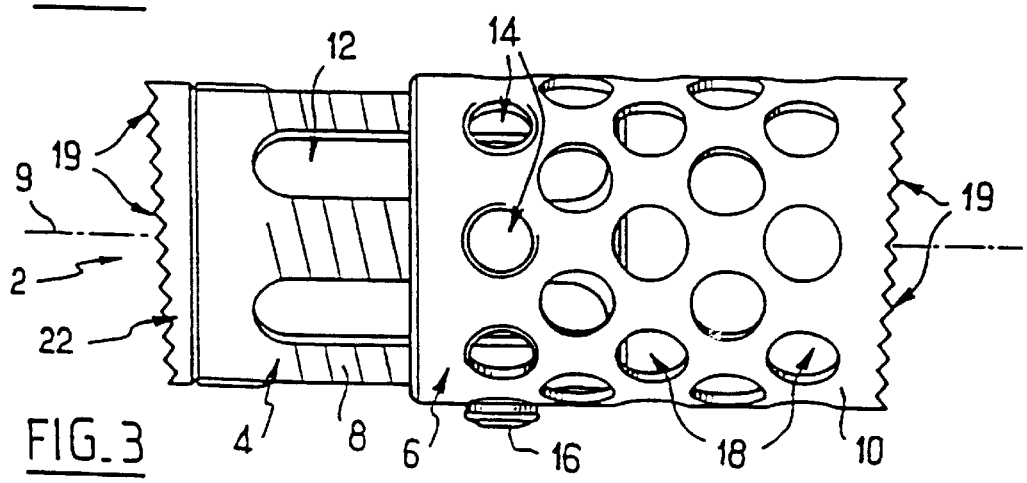
FIG_3

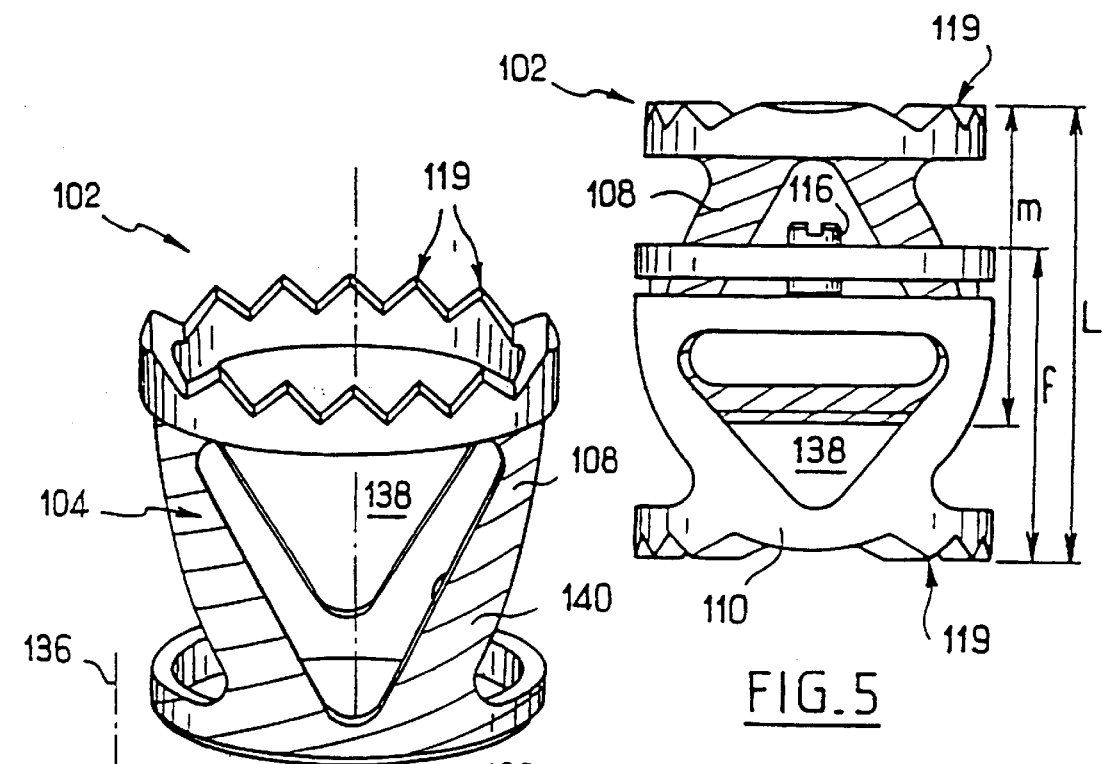
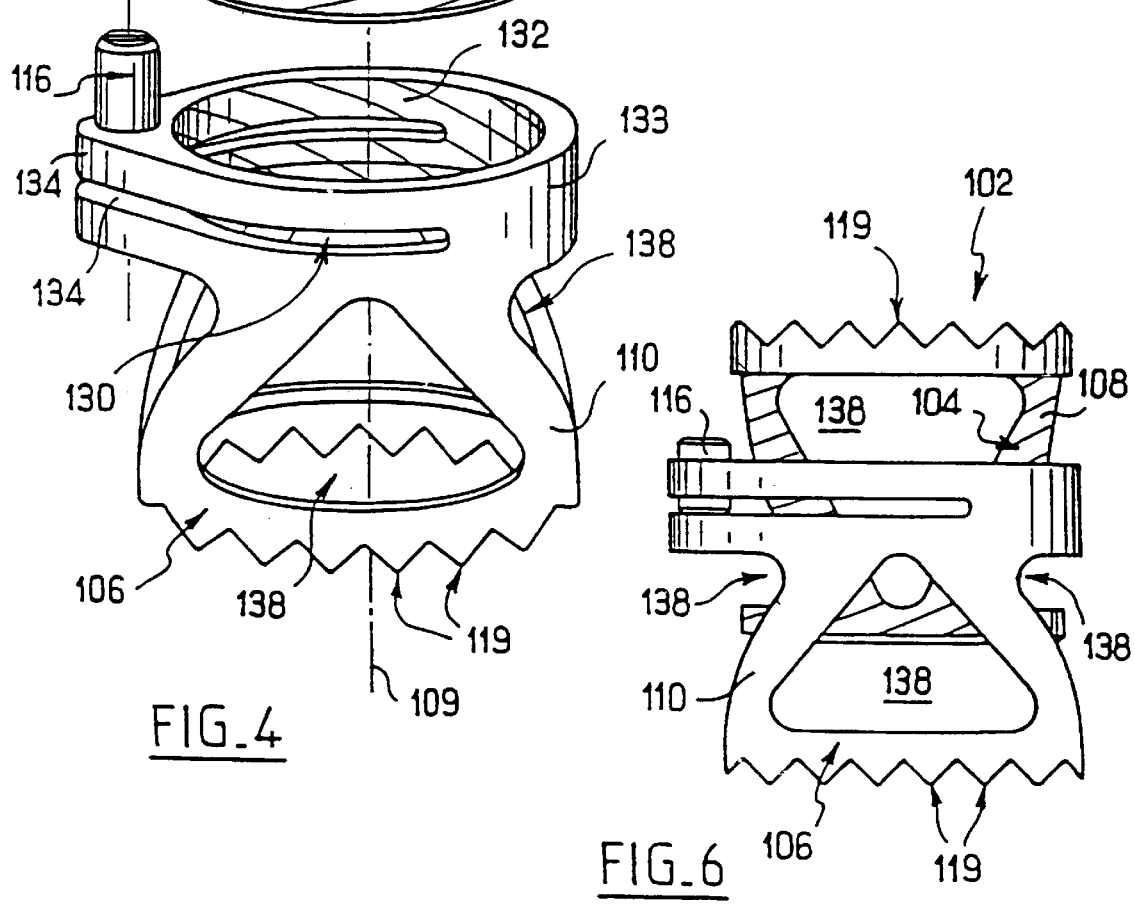

US 6,616,695 B1

IMPLANT FOR REPLACING A VERTEBRA

BACKGROUND OF THE INVENTION

Field of the Invention

The invention relates to implants for replacing at least part of a vertebra, for example after ablation of the vertebra.

The document EP-0 567 424-A1 discloses an implant of this kind comprising an intermediate body and two bearing parts adapted to bear against the vertebral plates of vertebrae adjacent the space left by a vertebra that has been removed. Each bearing part is assembled to one end of the intermediate body by a screw connection so that rotation of each bearing part relative to the body varies the total length of the implant. However, it takes a relatively long time to assemble the various components of the implant. What is more, given the number of parts capable of relative movement, adjusting the length of the implant is relatively complicated and takes a long time, which increases the duration of the surgery. Finally, manufacturing the implant entails defining a large number of accurate surfaces enabling relative movement of the parts. Manufacture is long and costly.

U.S. Pat. No. 5,723,013 relates to an implant for replacing a vertebra that is made up of two implant parts sliding one within the other. The two parts are in mutual contact through teeth enabling the length of the implant to be increased by distraction of the two parts. The length cannot be reduced, however. The length of the implant can be adjusted simply and quickly. However, fine adjustment of the length of the implant is not possible.

An object of the invention is to provide an implant that is quick to install during surgery and that enables fine adjustment of its length.

To achieve the above object, the invention provides an implant for replacing at least part of a vertebra, the implant having two parts adapted to be joined together and enabling a total dimension of the implant to be adjusted, each part having a fixed dimension homologous to the total dimension of the implant, characterized in that the parts form a screw connection with each other.

Accordingly, during surgery, the total dimension of the implant is adjusted by moving only the two parts of the implant relative to each other. Adjustment is therefore simple and fast. Similarly, assembling the mobile parts of the implant before or during the operation is simple and fast. What is more, the number of surfaces enabling relative movement of the parts is reduced. Because the surfaces concerned are very accurate surfaces, fabrication of the implant is easy and its cost is low. The screw connection enables fine adjustment of the length of the implant.

At least one of the parts is advantageously in one piece.

This further reduces the number of parts to be assembled.

At least one of the parts is advantageously in more than one piece.

This facilitates obtaining some shapes of the part concerned.

Each part advantageously has at least one lateral opening and the openings can be superposed to receive a fixing member.

This facilitates superposing the openings, in particular when the two parts are relatively mobile by virtue of a screw connection.

SUMMARY OF THE INVENTION

At least one of the openings is advantageously elongate.

The elongate opening is advantageously rectilinear and parallel to a direction of measuring the total dimension of the implant.

One part advantageously has an elongate opening and the other part advantageously has at least one circular opening.

One part is advantageously a female part adapted to receive the other part and including a body and a flange which can be moved relative to the body to immobilize the other part by wedging it.

Accordingly, the wall of at least one of the two parts does not necessarily have to have an orifice to receive a member for fixing the two parts together. The wall of each part can therefore be apertured as much as may be required to show the implant clearly on X-rays and to favor the growth of bone with a view to its osteointegration.

The flange is advantageously mobile by virtue of elastic deformation of the female part.

The flange and the body advantageously each have a conduit to receive a member positioning the flange relative to the body.

The conduits are advantageously parallel to a direction in which the other part is received into the female part.

The flange advantageously comprises an uninterrupted collar.

The collar is advantageously in a plane perpendicular to a direction in which the other part is received into the female part.

At least one of the parts advantageously has a toothed end forming an end of the implant.

Other features and advantages of the invention will become apparent in the course of the following description of two preferred embodiments of the invention, which description is given by way of non-limiting example only. In the accompanying drawings:

BRIEF DESCRIPTION OF THE DRAWINGS

FIGS. 1 and 2 are perspective views of a first embodiment of an implant according to the invention respectively before and after assembly;

FIG. 3 is a side view of one variant of the first embodiment;

FIG. 4 is a perspective view of a second embodiment of an implant according to the invention before assembly; and FIGS. 5 and 6 are two side views of the implant shown in FIG. 4 after assembly.

DESCRIPTION OF THE PREFERRED EMBODIMENTS

Referring to FIGS. 1 and 2, in a first embodiment of the invention the implant 2 has two parts 4, 6.

Each part 4, 6 includes a cylindrical tubular one-piece body 8, 10 that has an axis 9. The body 8, also referred to as the male body, is adapted to penetrate into the body 10, also referred to as the female body, in a direction parallel to the axis 9. The male body 8 is threaded externally and the female body 10 is threaded internally to cooperate with the male body and provide a screw connection. A side wall of the male body 8 has identical rectilinear elongate openings or slots 12 of constant width that are parallel to each other and to the axis 9. Each extends more than half the length of the body 8 in a direction parallel to the axis 9. They are distributed all around that axis. A side wall of the female body 10 has a series of circular fixing openings or slots 14 that are identical to each other and lie in a common plane perpendicular to the axis 9 and in the vicinity of a proximal edge of the female body through which the male body 8 penetrates into the female body 10. The circular openings 14 are threaded. The diameter of the circular openings 14 is equal to the width of the elongate openings 12. The female part 6 has a fixing screw 16 adapted to cooperate with the circular openings 14 to provide a screw connection.

The female body has an end wall including circular openings 18 at a distal edge of the female body that is opposite the proximal edge in the axial direction 9. The distal edge of the female body has teeth 19 extending away from the proximal edge. The wall of the female body 10 has other circular openings 18 which are not threaded between the distal edge and the fixing openings 14.

The wall of the male body 8 has an internal thread in the vicinity of a distal edge opposite the proximal edge adapted to penetrate into the female body. The male part 4 includes a cap 22 comprising a threaded cylindrical wall for fixing it by means of a screw connection to the threaded distal edge of the male body. The cap 22 has an end wall perpendicular to the axis 9 and including circular openings 18 and teeth 19 directed away from the male body 8. The threads of the cap 22 and of the distal edge of the male body 8 are just long enough to rigidly fix the cap 22 onto the male body 8 in an axial abutting relationship so that the cap can be separated from the body 8 by very slightly rotating it about the axis 9, for example by rotating it through one or two turns. When the cap 22 is not abutted on the distal edge it is connected to the body 8 with play. The various positions of the cap 22 relative to the body 8 when their threads are in mesh do not significantly change the length of the male part 4 along the axis 9 because the threads have a very small inclination to the axis 9. The male and female parts have respective fixed lengths m and f parallel to the axis 9.

To assemble the implant 2, the cap 22 is fixed to the body 8 to constitute the male part 4. The male part 4 is then inserted in the female part 6 with their respective threads meshing. Both threads are very long to provide a wide choice as to the length over which the male part 4 penetrates into the female part 6. Because of the screw connection, relative rotation of the male and female parts adjusts the total length L of the implant in the direction parallel to the axis 9. The length L corresponds to the distance between the two vertebral plates between which the implant is to be installed. When the length L suited to the intervertebral space to be occupied is obtained, the screw 16 is inserted in one of the fixing openings 14 in the female body 6 which coincides with an elongate opening 12 in the male body 4. If there is no such coincidence, all that is required to bring about such coincidence is to turn the two parts relative to each other by a very small fraction of one turn, thanks to the elongate shape of the openings 12. The screw 16 is inserted as far as the corresponding elongate opening 12, which prevents subsequent relative rotation of the two parts. Finally, the screw 16 is tightened until its head bears against the female body 6. The adjustment of the distance L and the fixing of the screw 16 are carried out at least in part with the implant 2 in situ, occupying the space left by the vertebra that has been partly or totally removed. The distal edges of the male and female parts then bear against the respective vertebral plates of two vertebrae adjacent the latter space. The teeth 19 ensure a good grip of the implant 2 on the plates and facilitate osteointegration of the implant. All the openings 12, 14, 18 of the implant facilitate osteosynthesis for the purpose of osteointegration.

In the FIG. 3 variant, the distal edges carrying the teeth are in planes inclined to the plane perpendicular to the axis 9 to allow for the inclined configuration of the vertebral plates of some vertebrae.

Referring to FIGS. 4 to 6, in the second embodiment, in which the reference numbers of corresponding components are increased by 100, the two parts 104, 106 of the implant provide a male-female coupling with a screw connection, as previously. Each distal edge and the teeth it carries are now in one piece with the corresponding body. The male part 104 is in one piece. The male part 104 and the female part 106 have no end walls and the ends of the implant associated with the distal edges are open.

The proximal edge of the female part 6 has a slot 130 in a plane perpendicular to the axis 109 and in the shape of a circular arc subtending an angle about the axis greater than 180°, for example equal to 200°. The slot 130 therefore delimits a flange 132 carrying the proximal edge and forming an uninterrupted circular collar which can move relative to the remainder of the body by elastic deformation of a junction part 133 connecting the remainder of the body to the flange. On either side of the slot 130, and opposite the junction part, the flange and the body have respective facing lobes 134 projecting from the outside face of the female body 106. The lobes 134 have respective conduits with a common axis 136 parallel to the axis 109. The female part includes a screw 116 adapted to be inserted through the flange 132 into the two conduits to engage with a thread of the conduit in the body 110, a head of the screw abutting on the lobe of the flange.

The lateral walls of the male and female bodies have triangular openings 138 that extend from one of the corresponding proximal and distal edges to the other. The triangular openings 138 on each male and female part are alternately inverted relative the axis 109 to define between them branches 140 connecting the distal edge to the proximal edge, both of which are circular and uninterrupted. These very large openings 138 ensure that the implant 102 is highly visible in X-rays and encourage osteointegration.

The length L of the implant is chosen by relative rotation of the two parts 104, 106, as previously. When the desired length L is reached, the screw 116 is tightened to move the flange 132 towards the body 106 by virtue of elastic deformation of the junction part 133. Because of the screw connection between the flange 132 and the male body 104 and the screw connection between the male body 104 and the female body 106, this movement over a very short distance achieves rigid wedging of the male and female parts relative to each other. Alternatively, the fixing by the screw 116 could be such that the wedging effect is achieved by movement of the flange 132 away from the female body 106.

The implant 2, 102 according to the invention enables a bone graft to be fitted between two vertebral plates when total or partial corporectomy and ablation of the overlying or underlying intervertebral discs have been carried out. Once adjusted to the size of the space to be filled, by choosing its length L, the implant 2, 102 is filled with bone, generally taken from the patient. This achieves a graft and braces the spinal column.

What is claimed is:

1. An implant for replacing at least part of a vertebra, the implant comprising two parts telescoping with respect to a longitudinal axis adapted to be threadably joined together and enabling a total dimension (L) of the implant to be adjusted each part having a fixed length, the two parts having respective male and female threads and forming a screw connection with each other, whereby said dimension L can be adjusted by the relative rotation of said two parts, each of the two parts respectively contacting first and second vertebral surfaces and an anti-rotation element engageable with both of said two telescoping parts to selectively prevent the relative rotation therebetween wherein said anti-rotation element is moveable in a direction transverse to said axis and a second part of said two parts has at least one slot opening therein and a first part of said two parts having a threaded opening therein and wherein said anti-rotation device is a screw threaded into said threaded opening of said first part extending into said slotted opening in said second part.

2. The implant according to claim 1, wherein at least one of the first and second parts is a unitary piece.

3. The implant according to claims 1 or 2, wherein at least one of the first and second parts has multiple pieces.

4. The implant according to claims 1 or 2, wherein the first and second cylindrical parts are tubular having walls, the walls of each part has at least one opening therethrough.

5. The implant according to claim 4, wherein at least one of the openings is elongate.

6. The implant according to claim 5, wherein the elongate opening has a longitudinal extent parallel to the longitudinal axis of the implant.

7. The implant according to claim 5, wherein one part has an elongate opening and the other part has at least one circular opening.

8. The implant according to claim 1, wherein at least one of the first ends of the first and second parts have teeth.

9. The implant according to claim 1, wherein said first and second parts have a cavity and openings connecting the cavity to the outside of the parts.

10. A spinal implant comprising:
   a first generally tubular part having a threaded inner surface and an end surface for contacting a first vertebra;
   a second generally tubular part having a threaded outer surface, said second part outer surface threaded into said threaded inner surface of said first part for relative movement between the parts along a longitudinal axis, said second part having an end surface for contacting a second vertebra; and
   an anti-rotation device connected to one of said first or second parts for selectively engaging the other of said first or second parts for selectively allowing or preventing relative rotation of said threaded surfaces said anti-rotation device moveable in a direction transverse to said longitudinal axis for said selective engagement wherein said second piece has at least one slotted opening therein and said first piece having a threaded opening therein and said anti-rotation device is a screw threaded into said threaded opening of said first piece and extending into said slotted opening in said second piece.

11. The implant as set forth in claim 10, wherein at least one of the first and second parts is an assembly of at least two parts.

12. The implant as set forth in claim 10, wherein each part has at least one opening formed in a wall of the part which opening can be superimposed to receive the anti-rotation device.

13. The implant as set forth in claim 12, wherein at least one of the openings is elongate.

14. The implant as set forth in claim 13, wherein the elongate opening extends parallel to said longitudinal axis.

15. The implant according to claim 13, wherein one part has an elongate opening and the other part has at least one circular opening.

16. The implant according to claim 10, wherein at least one of the parts has teeth formed on said end surface for contacting a vertebra.

17. An implant according to claim 10, wherein first and second parts have an inner cavity defined by walls and openings in the walls connecting the cavity to the outside of the implant.

18. The implant as set forth in claim 10, wherein said anti-rotation device is a set screw mounted on one of said parts and engageable with the other of said parts.

19. A method for replacing at least part of a vertebra in a human spine, comprising:
   forming an opening in the spine by removing at least part of a vertebra, said removing of said vertebra leaving facing bone surfaces;
   inserting a two piece telescoping implant having an end on a first piece and an end on a second piece for engaging said vertebral facing bone surfaces into said opening, said implant first piece having a female part with a threaded inner surface and said second piece having a male part with a threaded outer surface threadably engaging the inner thread of the female part for relative movement along a longitudinal axis;
   adjusting the length of the implant to match a height of said opening between the facing bone surfaces along said longitudinal axis by rotating the first piece female part with respect to the second piece male part; and
   locking said implant at the adjusted length by activating an anti-rotation device connected to one of said male or female parts for selectively engaging the other of said male or female parts to prevent rotation therebetween said locking element moveable in a direction transverse to said longitudinal axis for said selective engagement wherein said second piece has at least one slotted opening therein and said first piece having a threaded opening therein and said anti-rotation device is a screw threaded into said threaded opening of said first piece and extending into said slotted opening in said second piece.

20. The method as set forth in claim 18, wherein the anti-rotation device connected to one of said parts is a set screw engaging an opening in the other of said parts.

21. The implant as set forth in claim 10, wherein said second piece has at least one opening therein and said first piece having a threaded opening therein and said anti-rotation device is a screw threaded into said threaded opening of said first piece and extending into said opening in said second piece.

22. The implant as set forth in claim 19, wherein said second piece has at least one opening therein and said first piece having a threaded opening therein and said anti-rotation device is a screw threaded into said threaded opening of said first piece and extending into said opening in said second piece.

23. The implant has set forth in claim 1, wherein said anti-rotation element is moveable in a direction transverse to said axis and a second part of said two parts has at least one opening therein and a first part of said two parts having a threaded opening therein and wherein said anti-rotation device is a screw threaded into said threaded opening of said first part and extending into said opening in said second part.

\* \* \* \* \*

UNITED STATES PATENT AND TRADEMARK OFFICE
CERTIFICATE OF CORRECTION

PATENT NO. : 6,616,695 B1
DATED : September 9, 2003
INVENTOR(S) : Yves Crozet and Christian Baccelli It is certified that error appears in the above-identified patent and that said Letters Patent is hereby corrected as shown below:

Title page,
Item [57], ABSTRACT,
Line 1, cancel "(2)".
Lines 2 and 6, cancel "(4, 6)".

Column 1,
Line 9, insert -- DESCRIPTION OF PRIOR ART --.

Column 2,
Line 10, "including" should read -- includes --.
Line 38, cancel "In".
Line 39, cancel "the accompanying drawings:".
Line 41, insert -- In the accompanying drawings: --.

Column 3,
Line 23, "including" should read -- includes --.

Column 4,
Line 15, "6" should read -- 106 --.
Line 42, after "previously" insert -- described --.
Line 66, after "adjusted" insert -- , --.

Column 5,
Line 18, "has" should read -- have --.
Line 28, "have" should read -- has --.
Line 45, after "surfaces" insert -- , --.

UNITED STATES PATENT AND TRADEMARK OFFICE
CERTIFICATE OF CORRECTION

PATENT NO.    : 6,616,695 B1
DATED         : September 9, 2003
INVENTOR(S)   : Yves Crozet and Christian Baccelli It is certified that error appears in the above-identified patent and that said Letters Patent is hereby corrected as shown below:

<u>Column 6,</u>
Line 59, "has" should read -- as --.

Signed and Sealed this

Twenty-third Day of December, 2003

JAMES E. ROGAN
*Director of the United States Patent and Trademark Office*